US 10,449,229 B2
Oct. 22, 2019

(12) United States Patent
Cowman et al.

(10) Patent No.: US 10,449,229 B2
(45) Date of Patent: Oct. 22, 2019

(54) COMPOSITIONS AND METHODS FOR CARTILAGE DEFECT REPAIR USING A RHAMM-MIMETIC PEPTIDE

(71) Applicants: New York University, New York, NY (US); London Health Sciences Centre Research Inc., London (CA)

(72) Inventors: Mary K. Cowman, Mohegan Lake, NY (US); Thorsten Kirsch, River Edge, NJ (US); Eric J. Strauss, New York, NY (US); Eva Ann Turley, London (CA); Cornelia Toelg, Vienna (CA); Leonard G. Luyt, London (CA)

(73) Assignees: New York University, New York, NY (US); London Health Sciences Centre Research Inc., London (CA)

( * ) Notice: Subject to any disclaimer, the term of this patent is extended or adjusted under 35 U.S.C. 154(b) by 56 days.

(21) Appl. No.: 15/504,938

(22) PCT Filed: Aug. 19, 2015

(86) PCT No.: PCT/US2015/045934
§ 371 (c)(1),
(2) Date: Feb. 17, 2017

(87) PCT Pub. No.: WO2016/028914
PCT Pub. Date: Feb. 25, 2016

(65) Prior Publication Data
US 2017/0239318 A1    Aug. 24, 2017

Related U.S. Application Data

(60) Provisional application No. 62/039,150, filed on Aug. 19, 2014.

(51) Int. Cl.
*A61K 38/10*    (2006.01)
*A61K 31/728*    (2006.01)
(Continued)

(52) U.S. Cl.
CPC ............ *A61K 38/10* (2013.01); *A61K 31/728* (2013.01); *A61K 35/28* (2013.01); *C07K 14/70585* (2013.01); *C07K 14/70596* (2013.01)

(58) Field of Classification Search
CPC .. A61K 31/728; A61K 2300/00; A61K 35/28; A61K 38/10; A61K 38/1891; A61K 45/06; A61K 35/32; A61K 31/726; A61K 38/00; A61K 31/7068; A61K 31/192; A61K 31/198; A61K 31/337; A61K 31/37; A61K 31/42; A61K 31/573; A61K 31/593; A61K 31/706; A61K 31/7076; A61K 31/7088; A61K 38/1825; A61K 38/1875; A61K 38/225; A61K 38/47; A61K 38/1709; A61K 38/385; A61K 38/45; A61K 47/60; A61K 31/01; A61K 31/167; A61K 31/202; A61K 36/00; A61K 36/02; A61K 36/10; A61K 38/17; A61K 38/1841; A61K 38/16; A61K 9/0019; A61K 38/08; A61K 31/175; A61K 31/352; A61K 31/365; A61K 31/40; A61K 31/4152; A61K 31/427; A61K 31/519; A61K 31/5377; A61K 31/551; A61K 31/5513; A61K 31/56; A61K 31/7048; A61K 31/7072; A61K 38/005; A61K 38/014; A61K 38/1703; A61K 38/191; A61K 39/3955; A61K 47/56; A61K 47/643; A61K 31/16; A61K 31/727; A61K 38/06; A61K 47/42; A61K 8/64; A61K 9/06; A61K 2039/505; A61K 2039/507; A61K 2039/545; A61K 31/00; A61K 31/445; C07K 14/515; C07K 14/47; C07K 2319/30; C07K 7/08; C07K 14/00; C07K 14/78; C07K 7/06; C07K 16/2827; C07K 16/3015; C07K 16/3046; C07K 16/40; C07K 2317/24; C07K 2317/32; C07K 2317/34; C07K 2317/53; C07K 2317/56; C07K 2317/565; C07K 2317/76; C07K 2317/94; C07K 14/70585; C07K 14/70596; C12N 2501/17; C12N 2506/1346; C12N 5/0655; C12N 9/003; C12N 9/2474; C12Q 1/6883; C12Q 2600/118; C12Q 2600/158; G01N 2333/78; G01N 2800/105; G01N 2800/52; G01N 33/6887; Y02A 50/463; Y02A 50/478; Y02A 50/481; C12Y 105/01003; C12Y 302/01035; C12Y 304/24035;
(Continued)

(56) References Cited

U.S. PATENT DOCUMENTS

2004/0034201 A1* 2/2004 Turley .................... C07K 7/08
530/388.22
2010/0143382 A1    6/2010 Turley et al.

OTHER PUBLICATIONS

Camillieri G et al: "Hyaluronan-Induced Stimulation of Corneal Wound Healing Is a Pure Pharmacological Effect" Journal of Ocular Pharmacology and Therapeutics, Mary Ann Liebert, Inc., New York, NY, US, vol. 20, No. 6, Jan. 1, 2004 (Jan. 1, 2004), abstract only.*

(Continued)

*Primary Examiner* — Deborah K Ware
(74) *Attorney, Agent, or Firm* — Hodgson Russ LLP

(57) ABSTRACT

Provided are methods and compositions for cartilage repair. The method involves performing a surgical procedure at the site of a cartilage defect and administering a composition comprising a receptor for hyaluronan mediated motility (RHAMM)-mimetic peptide, and a high molecular weight hyaluronan.

10 Claims, 8 Drawing Sheets

Specification includes a Sequence Listing.

(51) Int. Cl.
*C07K 14/705* (2006.01)
*A61K 35/28* (2015.01)
(58) Field of Classification Search
CPC .... A23K 20/158; A23K 20/174; A23K 20/30; A23K 50/40; A23L 33/10; A23L 33/12; A23L 33/15; A23L 33/16; A23L 33/175; A61L 27/227; A61L 27/3604; A61L 27/3641; A61Q 19/08
See application file for complete search history.

(56) References Cited

OTHER PUBLICATIONS https://www.thesteadmanclinic.com/patient-education/knee/microfracture-technique, 2018.*
Merriam-Webster Medical Dictionary at https://www.merriam-webster.com/medical/microfracture, 2009.*
Tanaka, N., et al., Intra-articular injection of high molecular weight hyaluronan after arthrocentesis as treatment for rheumatoid knees with joint effusion, Rheumatology International, Jun. 26, 2002, vol. 22, No. 4, pp. 151-154.

* cited by examiner

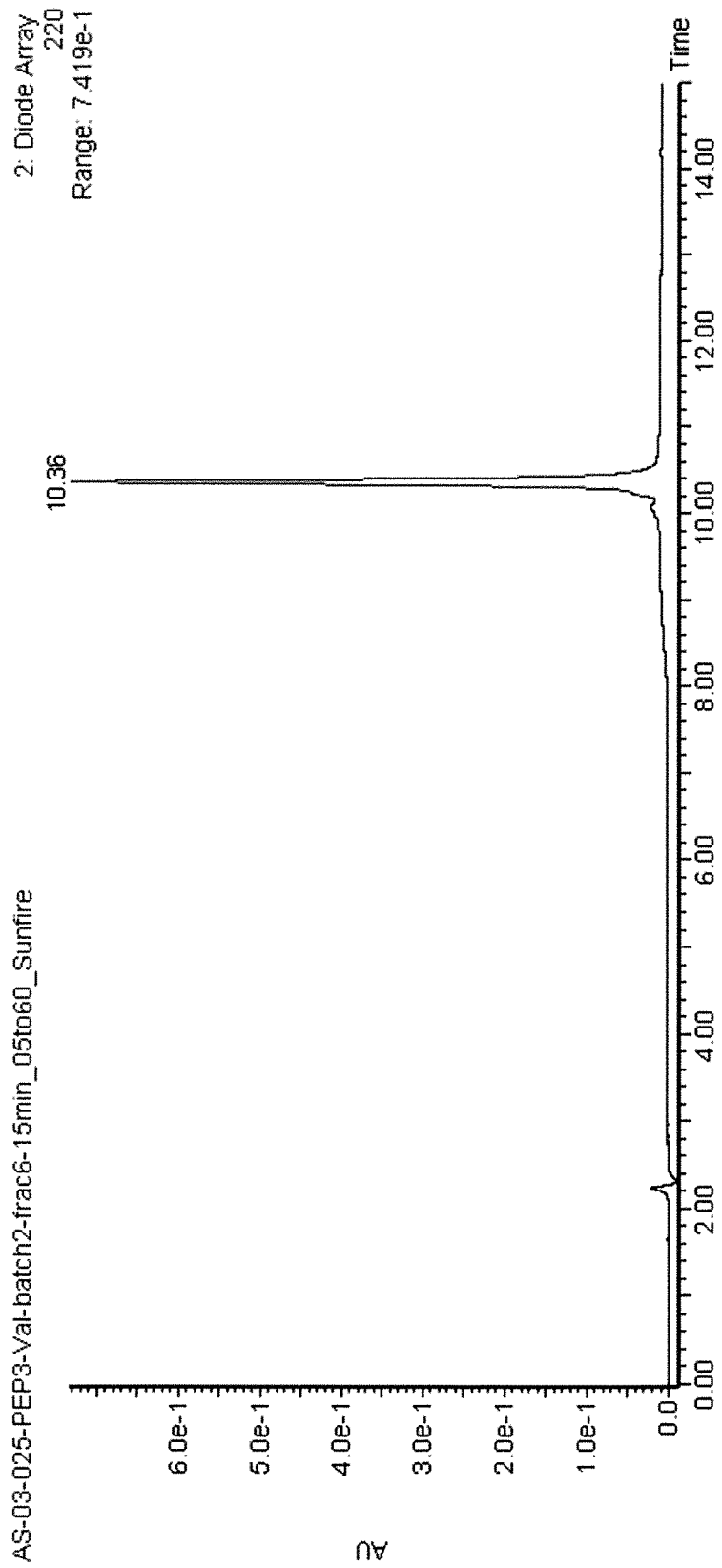
FIG. 1A    H-STMMSRSHKTRSHHV-OH (SEQ ID NO: 1)

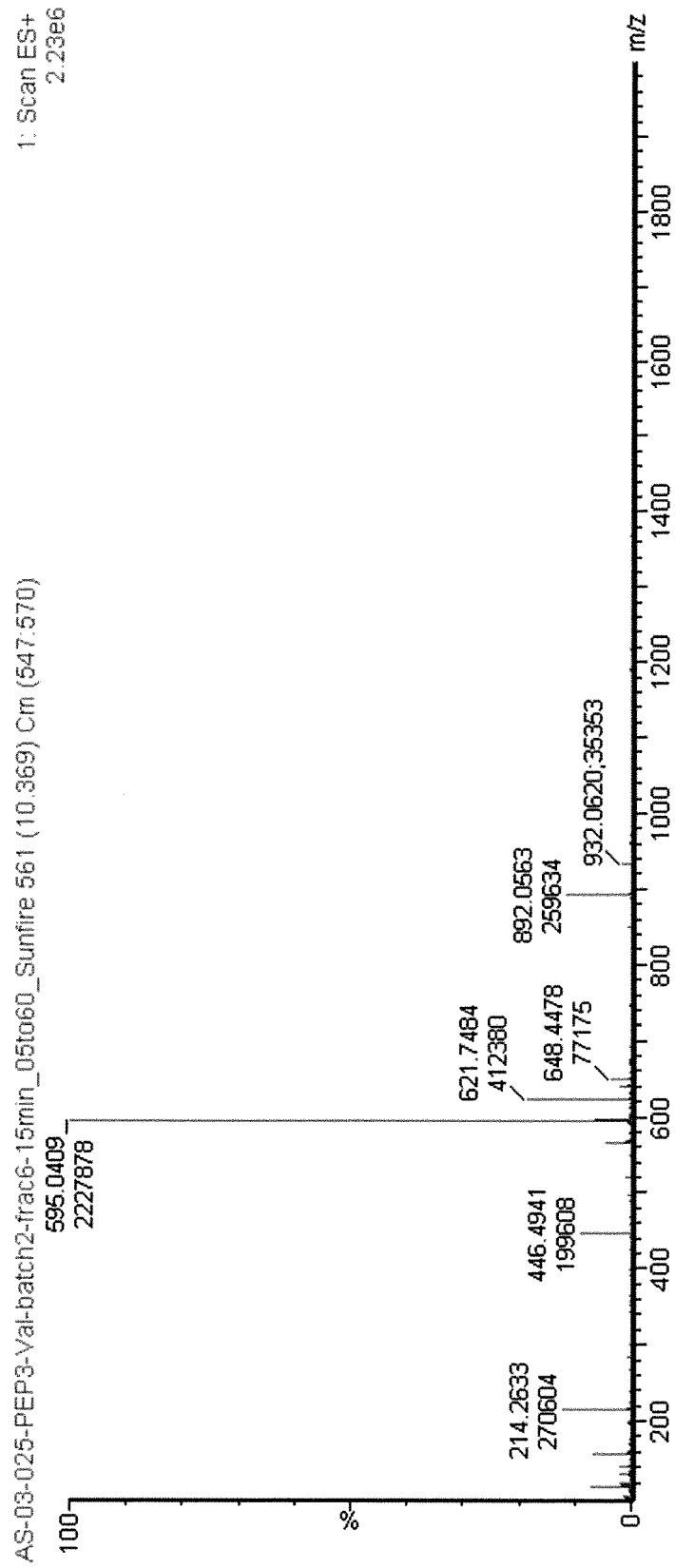
FIG. 1B  H-STMMSRSHKTRSHHV-OH (SEQ ID NO: 1)

SEQUENCE LISTING

```
<160> NUMBER OF SEQ ID NOS: 1

<210> SEQ ID NO 1
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE
```

-continued

```
<400> SEQUENCE: 1

Ser Thr Met Met Ser Arg Ser His Lys Thr Arg Ser His His Val
1               5                   10                  15
```

COMPOSITIONS AND METHODS FOR CARTILAGE DEFECT REPAIR USING A RHAMM-MIMETIC PEPTIDE

CROSS-REFERENCE TO RELATED APPLICATIONS

This application claims priority to U.S. provisional patent application No. 62/039,150, filed on Aug. 19, 2014, the disclosure of which is incorporated herein by reference.

STATEMENT REGARDING FEDERALLY SPONSORED RESEARCH

This invention was made with government support under grant number UL1 TR000038 from the National Institutes of Health. The government has certain rights in the invention.

FIELD OF THE DISCLOSURE

This disclosure relates generally to the field of cartilage repair and more particularly to compositions and methods for repair of cartilage defects by combination of surgical manipulation and administration of compositions comprising receptor for hyaluronan-mediated motility (RHAMM)-mimetic peptides.

BACKGROUND OF THE DISCLOSURE

Injury to articular cartilage is common; one study of 31,516 knee arthroscopies found that 63% of patients had at least one chondral injury present at the time of surgery, irrespective of their surgical indication (1). Cartilage injuries of the knee affect approximately 900,000 Americans annually, resulting in more than 200,000 surgical procedures (2). These injuries are frequently associated with pain, diminished joint functionality, and reduced quality of life. Due to the tissue's lack of intrinsic healing ability, traumatic joint injuries are often followed by formation of poorly repaired cartilage defects that lead to the early onset of osteoarthritis, which requires eventual joint replacement. Joint replacement, especially at a relatively young age, results in significant limitations to lifestyle, as well as potential complications. More importantly, joint replacement in a young patient group is complicated by the limited lifespan of the implants and the eventual requirement for revision surgery (3).

Articular cartilage is an avascular tissue that has no intrinsic capacity to heal or repair because of the lack of chondrocytic precursor cells. Surgical reparative techniques to repair cartilage injuries include marrow stimulation or microfracture, cell-based restorative techniques, and osteochondral allografts and autografts (2). Despite the refinement and advancement of these surgical techniques, full-thickness chondral defects still remain a major challenge, because none of the surgical methods, including the cell-based approaches, form hyaline cartilage. Thus, the common term used in the literature is 'hyaline-like' repair tissue. Since the function of articular cartilage is intrinsically linked to its structure, the benefits, characteristics and durability of this 'hyaline-like' cartilage tissue remains unknown. Currently, the two most common procedures being used to repair cartilage are the microfracture technique and the implantation of autologous in vitro expanded chondrocytes into the cartilage defect (2). The microfracture technique relies on the stimulation of the bone marrow to release mesenchymal stem cells that migrate into the lesion site, where these precursor cells differentiate into articular chondrocytes that produce an extracellular matrix that restores cartilage. Unfortunately, these precursor cells differentiate into fibro-chondrocytes that make fibrocartilage, a tissue with inferior biochemical and biomechanical properties compared to hyaline cartilage. Consequently, this intervention is reasonably successful in the short- and mid-terms (months to a few years) but fails in the long-term (2). In Mithoefer's systematic review of 28 clinical studies, a significant deterioration in outcomes was noted to be present two years following microfracture, secondary to the limited amount of hyaline cartilage that forms following the procedure (28). Autologous chondrocyte implantation has been shown to lead to the formation of a more hyaline-like cartilage structure, which is still far from being hyaline cartilage and therefore the successful long-term outcome of this type of approach is also questionable. In addition, this procedure is markedly more costly than the microfracture technique, requires open surgery instead of arthroscopic surgery, and involves two surgical procedures (4). The first surgery involves a cartilage tissue biopsy from a non-weight bearing area, while the second surgery is the actual repair surgery. Chondrocytes can be isolated from the harvested cartilage tissue biopsy and expanded in vitro (4). Expansion of chondrocytes in vitro is challenging and problematic, since these cells often dedifferentiate into a fibroblast-like phenotype in culture (5). In addition, this procedure involves the suturing of a collagen I/III bilayer to the border of the articular cartilage lesion, into which a suspension of autologous chondrocytes is then injected. A recent study has shown that suturing of articular cartilage induces severe local damage that is progressive and reminiscent of that associated with the early stages of OA (6). Therefore, the improvement or development of novel procedures or the identification of novel biological factors that prevent fibrocartilage formation and promote the formation of hyaline cartilage are highly warranted.

Hyaluronan (HA) is a key macromolecular component of the joint synovial fluid that provides viscoelastic protection and lubrication of the cartilage surfaces (7-9). In osteoarthritis (OA), HA can be degraded to lower molecular weight HA fragments, providing less effective shock absorption and lubrication (10) A leading approach to treatment of OA is intra-articular injections of high molecular weight HA. Injected HA provides analgesia over a period of weeks or months, despite the fact that the soluble HA is washed out of the joint within a few days. Hyaluronan preparations containing chemically cross-linked HA gels are also used for prolonged residence in the joint, with similar symptomatic relief. The prolonged effect in both cases suggests a favorable but temporary modification of processes that lead to pain. These HA therapeutic preparations are not truly disease modifying, and invasive joint replacement surgery remains the ultimate treatment (11-15).

SUMMARY OF THE DISCLOSURE

The present disclosure provides compositions and methods for repair of cartilage defects. The compositions comprise high molecular weight hyaluronan (referred to as high molecular weight HA, HMWHA, or HMW hyaluronan) and a RHAMM-mimetic peptide. The RHAMM-mimetic peptide may have from 15 to 30 amino acids and may comprise or consist of the sequence of SEQ ID NO:1. The ratio of RHAMM-mimetic peptide and HMWHA in the composition can be from 1:10 to 1:1000 by weight. For example, the ratio can be from 1:10 to 1:100. The concentration of HMWHA can be from 1 mg/ml to 40 mg/ml, or 10 mg/ml to 20 mg/ml.

The concentration of the RHAMM-mimetic peptide in the composition can be from 5 µg/ml to 3 mg/ml, or from 10 µg/ml to 1 mg/ml.

The present disclosure also provides methods for repairing defects in a joint cartilage in a subject. The method comprises performing a surgical procedure at the site of a joint cartilage defect and administering a composition comprising a RHAMM-mimetic peptide to the site of the cartilage defect, or administering a RHAMM-mimetic peptide in combination with a high molecular weight HA, either combined or separately. For example, the composition—whether as a single composition or separate compositions comprising the RHAMM-mimetic peptide and the high molecular weight HA—may be administered at the time of the surgical procedure, immediately after performing a surgical procedure, or as some time following the surgical procedure. An example of a surgical procedure is microfracture. Alternatively, or additionally, the compositions may be administered at a desired time after the surgical procedure is performed.

BRIEF DESCRIPTION OF THE FIGURES

FIGS. 1A and 1B Representation of mass spectrometry analysis and HPLC analysis of a RHAMM-mimetic peptide of SEQ ID NO:1 (also referred to herein as peptide 15-1).

DESCRIPTION OF THE DISCLOSURE

Figure 2:
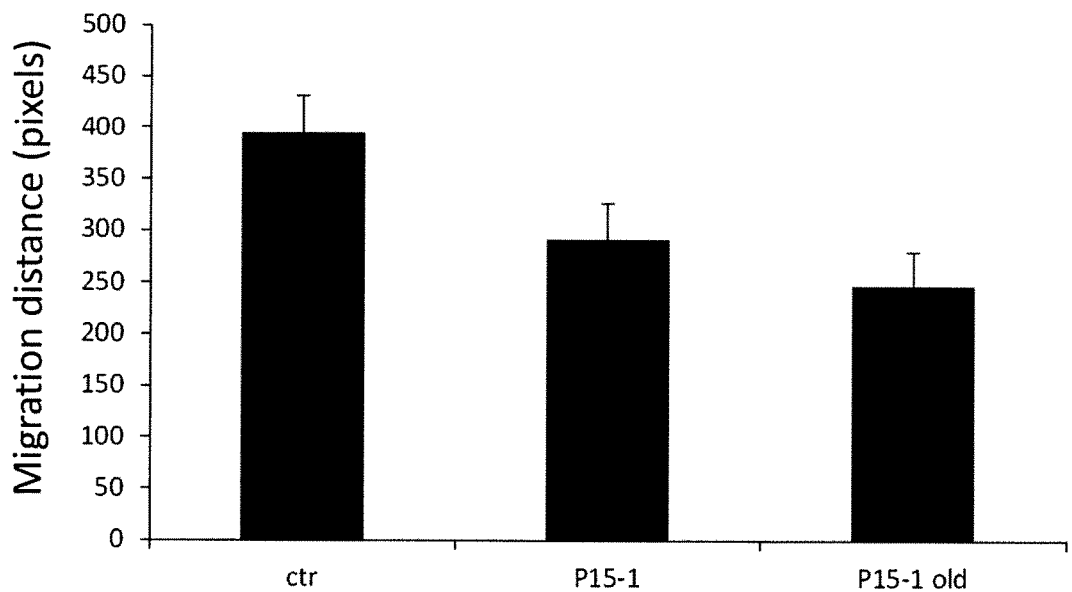
FIG. 2: Effect of peptide 15-1 on fibroblast migration, using an in vitro random motility assay. RHAMM overexpressing LR21 cells were plated on a fibronectin-coated surface in Dulbecco's Modified Eagles Medium (DMEM) with 10% fetal bovine serum (FBS). The following day medium was changed to DMEM with 1% FBS, 50 µg/ml peptide, 500 ng/ml 30-mer HA fragment. Random motility was measured microscopically. "Old P15-1" refers to a peptide batch that was used in previous experiments. As control (ctr), PBS was used instead of peptide.

This disclosure provides compositions and methods for repair of cartilage defect. The compositions comprise a peptide that can modulate hyaluronan signaling through receptor for hyaluronan-mediated motility (RHAMM). Thus, the composition can comprise a peptide mimic of RHAMM (referred to herein as a RHAMM-mimetic peptide), and optionally, high molecular weight hyaluronan (HA).

The term "high molecular weight hyaluronan" (HM-WHA, HMW hyluronan, or high molecular weight HA) as used herein means HA of average molecular weight of at least 500 kDa. All average molecular weights for HA in this disclosure are weight average molecular weights.

The term "RHAMM-mimetic peptide" as used herein means a peptide having a structure that mimics an HA binding domain of RHAMM.

The disclosure also provides a method for repairing defects in cartilage. The method comprises surgical manipulation of the cartilage and concurrent and/or subsequent administration of a therapeutically effective amount of a composition comprising a compound that decreases or inhibits signaling by RHAMM, and/or that decreases the rate of fibrosis. A therapeutically effective amount is the amount that—whether administered in a single administration or over multiple administrations—provides the desired result of ameliorating one or more symptoms or markers of the indication being treated. The composition can be administered to the area of defect, such as by intra-articular injection. The administered compositions comprises a RHAMM-mimetic peptide.

The present disclosure provides compositions comprising a RHAMM-mimetic peptide and high molecular weight HA. The hyaluronan useful for the present disclosure has an average molecular weight of at least 500 kDa. For example, the HA for the present disclosure has an average molecular weight in a range of 500 kDa to 10,000 kDa (and all integer values therebetween). The HA can have average molecular weight of 500, 1,000, 1,500, 2,000, 2500, 3,000, 3,500, 4,000, 4,500, 5,000, 5,500, 6,000, 6,500, 7,000, 7,500, 8,000, 8,500, 9,000, 9,500, and 10,000 kDa. For example, the HA can have an average molecular weight in the range of 1,000 to 8,000 kDa. The HMWHA may be modified or cross-linked. For example, HMWHA may be modified by covalent attachment to one or more heavy chains of inter-α-inhibitor (IαI), pre-α-inhibitor (PαI) or other molecules.

The RHAMM-mimetic peptide of the present disclosure can be from 15-30 amino acids and comprises the sequence STMMSRSHKTRSHHV (SEQ ID NO:1). Thus the peptide may consist of the sequence of SEQ ID NO:1, or may have 1-15 amino acids in addition to the sequence of SEQ ID NO:1. The additional amino acids may be added to the C-terminus, to the N-terminus or both. For example, this disclosure includes peptides that are 15, 16, 17, 18, 19, 20, 21, 22, 23, 24, 25, 26, 27, 28, 29 and 30 amino acids long that comprise the sequence of SEQ ID NO:1.

This 15-mer RHAMM-mimetic peptide of SEQ ID NO:1 blocks interaction of HA fragments with RHAMM. This peptide specifically mimics RHAMM since it markedly reduced binding of HA fragments to recombinant RHAMM but not to recombinant CD44. In healing of excisional skin wounds in a rat model, this RHAMM-mimetic peptide was shown to block signaling by HA fragments, and to lead to a regenerative type of healing with reduced fibrosis (16) The RHAMM-mimetic peptide, when applied once to a full-thickness excisional rat wound, reduced macrophage number, fibroblast number, and blood vessel density compared to scrambled, negative control peptide. It also promoted a form of scarless healing. It was shown that this peptide altered wound repair in wild type mice but not in RHAMM−/− mice, clearly indicating that fibrosis during skin repair is caused by the interaction of HA fragments with RHAMM and signaling through this receptor.

RHAMM-mimetic peptides may be prepared by methods well known in the art. For example, the peptides may be prepared by chemical synthesis, such as by using solid phase synthesis, or synthesis in homogenous solution. The peptides may also be prepared by recombinant DNA techniques. Synthesis of the RHAMM-mimetic peptides is described in US Patent Application Publication 2014/0179616. Hyaluronan is commercially available, such as from DePuy Mitek.

The present compositions comprising the RHAMM-mimetic peptide, or the RHAMM-mimetic peptide and HMWHA, can be provided in pharmaceutically acceptable carriers. Such carriers include, for example physiological buffers—such as phosphate buffered saline or other isotonic aqueous buffers. The carriers may also contain adjuvants, fillers, diluents, agar, pectin, oils, and/or other agents such as antibiotics, anti-viral agents and other therapeutic agents, carbohydrates including sorbitol, mannitol, starch, sucrose, dextrin and glucose, proteins such as albumin or casein, and buffers like alkaline phosphates. Carriers may also include autologous or allogenic plasma or serum, platelet rich plasma, and the like.

The RHAMM-mimetic peptide and the HMWHA may be administered in a single composition or in separate compositions, simultaneously or sequentially. When administered as a combined composition, the RHAMM-mimetic peptide and the HA can be well distributed in the formulation. Uniform distribution of RHAMM-mimetic peptide and HMWHA in a pharmaceutically acceptable carrier may be accomplished by proper mixing of the formulation prior to administration.

The concentration of HMWHA in the composition can be from 1 mg/ml to 40 mg/ml. For example, the concentration of HMWHA can be from 10 mg/ml to 30 mg/ml, or from 10 mg/ml to 20 mg/ml, or 10, 11, 12, 13, 14, 15, 16, 17, 18, 19 or 20 mg/ml. The ratio of RHAMM-mimetic peptide or peptides to HA may be in the range of 1:1 to 1:10,000 (and all ratios therebetween) by weight. For example the ratio of RHAMM-mimetic peptide to HMWHA (by weight) can be from 1:10 to 1:1,000 (and all ratios therebetween), or from 1:10 to 1:100 (and all ratios therebetween), or from 1:40 to 1:80, or from 1:50 to 1:70, (and all ratios therebetween) or 1:50, 1:55, 1:60, 1:65, or 1:70. If more than one RHAMM-mimetic peptide comprising SEQ ID NO:1 (such as different length peptides) are present, then the total amount of the peptide in the composition, or any ratio reflects the cumulative amount of all of such peptides. The concentration of RHAMM-mimetic peptide can be from 5 µg/ml to 3000 µg/ml. The concentration of the peptide can be dictated by the HMWHA concentration and the ratio of the peptide to HMWHA. For example, if HMWHA is present from 10-20 mg/ml, and the weight ratio of the peptide to HMWHA is from 10-100, then the peptide could be in the concentration range of 100-2000 µg/ml. For example, the peptide can be present from 10 µg/ml to 1 mg/ml. For HMWHA at 12 mg/ml, and weight ratio of the peptide to HMWHA at 1:60 (by weight), the peptide would be 200 µg/ml. For HMWHA at 1 mg/ml, and a peptide to HMWHA ratio of 1:60 (by weight), the peptide is about 16.7 µg/ml.

In the method of the present disclosure, a surgical procedure is carried out at the site of the defect. For example, debridement of cartilage at the defect site can be carried out to expose subchondral bone followed by microfracture to create tunnels through the subchondral bone to connect the defect site with the bone marrow. Instead of microfracture, the surgical procedure can be autologous chondrocyte transplantation, or mosaicplasty. Further, autologous mesenchymal stem cells (MSCs), such as those which are expanded ex vivo can be reintroduced into the individual at the site of the defect.

Following the surgical procedure, the composition comprising a RHAMM-mimetic peptide comprising or consisting of the sequence of SEQ ID NO:1, or a composition comprising a RHAMM-mimetic peptide comprising or consisting of the sequence of SEQ ID NO:1 and high molecular weight HA can be delivered to the site of the defect, such as by direct injection to this site, arthroscopically, or intra-articularly. The RHAMM-mimetic peptide comprising the sequence of SEQ ID NO:1 and HMWHA can be administered as a combined formulation or as separate formulations. A desired amount of the composition may be delivered in a single administration or via multiple administrations at one time or over a period of time. The amount administered to the site of defect can be determined by one skilled in the art depending upon the defect, the age of the individual, etc. For example, an amount of 0.5 to 10.0 mls (and all values therebetween to the tenth decimal place), can be administered. For example, 1 to 6 ml or 1 to 2 ml of the composition can be administered in a single injection. The administration may comprise 0.2 mg peptide and 12 mg HMWHA per ml of the composition. The injections can be carried out weekly or as needed.

In this disclosure we demonstrate regenerative repair of a full thickness defect in cartilage using microfracture surgery combined with intra-articular administration of a high molecular weight HA in conjunction with a RHAMM-mimetic peptide. In various aspects and embodiments, methods and compositions are provided. The present compositions and methods can be used for treatment of traumatic injuries to joints. For example, the present compositions and methods can be used for treatment of cartilage defects, including cartilage lesion. The improvement in healing is expected to reduce the incidence of post-traumatic osteoarthritis.

In one embodiment, this disclosure provides regenerative repair of cartilage injury by microfracture surgery combined with multiple intra-articular injections of a therapeutic formulation containing high molecular weight hyaluronan and a RHAMM-mimetic peptide, to modulate hyaluronan fragment effects on cell behavior, resulting in healing. The healing may occur without fibrosis or with reduced fibrosis. The present compositions and methods may be used for various indications including treatment for injuries to joints, for regenerative healing and avoidance of fibrosis. These compositions and methods would be particularly relevant to sports injuries or warfighter injuries.

The present methods and compositions may be used to alleviate or treat cartilage defect such as full thickness defect in the cartilaginous component of an articular joint or any other joint of a human subject. In one embodiment, the methods and compositions may be used to treat cartilage defect in non-human animals, including horses, cows, goats, sheep, dogs and the like.

While not intending to be bound by any particular theory, it is believed that during cartilage repair HA fragments bind to RHAMM on chondrocytic precursor cells or chondrocytes promoting the differentiation or de-differentiation of these cells into a fibroblastic phenotype resulting in the formation of fibrocartilage instead of hyaline cartilage. Consequently, interfering with binding of HA fragments to RHAMM will prevent the differentiation of chondrocytic precursor cells and/or the dedifferentiation of chondrocytes into fibroblast-like cells preventing the formation of fibrocartilage during cartilage repair.

The following examples are provided to further illustrate the invention. They are not intended to be limiting in any way.

EXAMPLE 1

We tested whether the 15-mer RHAMM-mimetic peptide (SEQ ID NO:1) permits modification of cartilage repair so as to improve outcome. Full-thickness cartilage defects were created in the weight bearing area of the medial femoral condyle in female sexually mature New Zealand White rabbits and further treated with surgical microfracture. Rabbits were randomly assigned to receive three weekly injections for the first three weeks after surgery with the RHAMM-mimetic peptide in a HMWHA solution (therapeutic agent) or HMWHA solution alone (control). At 3 months post-microfracture, the animals were sacrificed and cartilage repair was determined grossly using a modified component of the International Cartilage Repair Society (ICRS) Cartilage Repair Assessment scoring scale, and histologically using the modified International Cartilage Repair Society (ICRS) histological cartilage scoring system (17, 18).

Materials

HMWHA, as a 15 mg/ml sterile solution in physiological saline (ORTHOVISC®, 2 ml per syringe) was purchased from DePuy Mitek. The HMWHA had been extracted from chicken combs and was labeled to have an average molecular weight of 1.0-2.9 million daltons.

Peptide 15-1 (STMMSRSHKTRSHHV, SEQ ID NO:1), a RHAMM-mimetic peptide, was synthesized, purified using preparative high-performance liquid chromatography, and then characterized by electrospray ionization (ESI+) mass spectrometry (FIGS. 1A and 1B). Synthesis was carried out on Rink amide methylbenzhydrylamine (MBHA) resin (0.1 mmol) using automated (APEX 396 auto-synthesizer) solid phase peptide synthesis involving Fmoc deprotection and amino acid coupling cycles. Fmoc deprotection was carried out using 20% piperidine solution in N,N-dimethylformamide (DMF) throughout the synthesis (5 and 20 minutes periods). All amino acid couplings were carried out using 3 equivalents of Fmoc-protected amino acid and 2-(1H-benzotriazol-1-yl)-1,1,3,3-tetramethyluronium hexafluorophosphate (HBTU), 6 equivalents of N,N-diisopropylethylamine (DIPEA) in DMF at 30 and 90 minutes intervals. After each deprotection and coupling step, the resin was washed repeatedly with DMF (3×) and dichloromethane (DCM) (3×). The peptide was cleaved from the resin and all protecting groups were removed using a solution of 88% v/v trifluoroacetic acid (TFA), 5% v/v water, 5% m/v phenol, 2% v/v triisopropyl silane (TIS) for 2-4 hours. The filtrate was collected, precipitated using cold tert-butyl methyl ether and pelleted via centrifugation at 3000 rpm at −5° C. for 10 minutes. Pellets were then dissolved in distilled-deionized water and lyophilized yielding a white powder. Analysis and purification of the peptide was performed using a 5-60% gradient solvent system consisting of 0.1% TFA in $H_2O$ (solvent A) and 0.1% TFA in $CH_3CN$ (solvent B) at a linear flow rate of 1.5 mL/min and 20 mL/min for analytical and preparative HPLC, respectively. Analytical HPLC was performed using a Waters Sunfire RP-C18 column (4.6 mm×150 μm, 5 μm), and preparative HPLC was performed using a Waters Sunfire OBD RP-C18 column (19.0 mm×150 mm, 5 μm). Absorbance was detected at wavelengths of 220 nm and 254 nm using a Waters 2998 Photodiode Array detector. During purification, fractions were collected, lyophilized, and analyzed by ESI-MS (Waters MICROMASS QUATTRO MICRO API™). Peptide 15-1 was found to have a retention time of 10.36 minutes corresponding to an observed m/z of 892.0563 (12%) for $[M+2H]^{2+}$ and 595.0409 (100%) for $[M+3H]^{3+}$. Calculated m/z's for $[M+2H]^{2+}$ and $[M+3H]^{3+}$ were 891.4365 and 594.6269 respectively.

Peptide 15-1 was dissolved in sterile phosphate-buffered saline at a concentration of 10 mg/ml. Based on the molecular weight of 2580 for the hepta-TFA (trifluoroacetate) salt of the peptide (molecular weight of 1782), the peptide concentration was 3.88 mM. The solution was aliquoted as 284 μl per vial (2.84 mg) and frozen. It was thawed just before formulation.

Methods

Functional Testing of Peptide 15-1 Using an In Vitro Random Motility Assay.

The functional testing of peptide 15-1 using an in vitro random motility assay was done essentially as previously described (16). Briefly, RHAMM over-expressing LR21 cells were plated at 7×10⁵ cells/well in fibronectin coated six-well plates using Dulbecco's modified Eagle's medium (DMEM) (Gibco BRL/Invitrogen, Carlsbad, Calif.) containing 10% fetal calf serum (FCS). Confluence of cell monolayers after 24 hours was between 80% and 90%. Cells were injured with a 2-mm single-edge scraper producing one injury/well. Cells were washed twice with PBS and incubated with DMEM plus 1% FCS, and 500 ng/mL 30-mer HA fragments. To block HA fragment-stimulated cell migration, 50 μg/mL of each peptide was added concomitantly with HA. Cell cultures were incubated for 24 hours at 37° C. and 5% $CO_2$. Following incubation, cells were fixed in 3.7% paraformaldehyde then stained with hematoxylin, and images of wounds were taken using a 4× objective (Nikon) attached to an inverted Nikon microscope equipped with Hoffman optics. The number of cells that had migrated into the scratch wounds was quantified using NIH image processing software ImageJ as follows. A box adjusted to reach each opposing edge of the wound was placed over 3 randomly assigned parts of each scratch wound and the numbers of cells within the box were counted. Experiments were conducted in triplicate so that the total sampling per condition was n=9. Statistically significant (p<0.05) differences were assessed by the unpaired Student's T-test method using Microsoft Excel Software (Redmond, Wash.). FIG. 2 shows that the reduction in fibroblast migration by peptide 15-1 was statistically significant relative to the control.

Formulation of Therapeutic Agent.

The therapeutic agent was formulated to deliver 6 mg of HMWHA and 0.1 mg of peptide 15-1 in a 0.5 ml intra-articular injection. It contained 15 μmole of HMWHA disaccharide repeating units and 0.04 μmole of peptide, or ca. 1 peptide per 375 HMWHA disaccharides. The control was formulated to deliver 6 mg HMWHA in a 0.5 ml intra-articular injection. All procedures were conducted using sterile technique in a laminar flow biosafety cabinet.

Peptide 15-1 solution was diluted from 10 mg/ml to 1 mg/ml by mixing 0.2 ml of the stock solution with 1.8 ml sterile PBS. The diluted solution was filtered using a 0.2 μm ACRODISC filter. A 1.5 ml portion of filtered peptide 15-1 at 1 mg/ml was mixed with 6 ml of the 15 mg/ml HA stock, stirred by hand, sealed and stored for one week at 4° C. Twelve sterile insulin syringes were each filled with 0.5 ml of the mixture, taking care to avoid air bubbles. Syringes were stored at 4° C. until use.

Control solution of diluted HMWHA was prepared in the same manner, using 1.5 ml of filtered sterile PBS in admixture with 6 ml of the 15 mg/ml HMWHA stock.

Creation and Treatment of Cartilage Defect.

The creation of a cartilage defect and the microfracture surgery in rabbits was performed essentially as previously described (19). In this Institutional Animal Care and Use Committee-approved study, 8 female New Zealand White rabbits weighing between 3.5 and 4.5 kg had a full thickness cartilage defect created in the weight bearing area of the medial femoral condyle. With the animal under general anesthesia, and with the use of a standard aseptic technique, the right knee was approached through a medial parapatellar incision with the patella dislocated laterally. A 4 mm full-thickness cartilage defect was created in the central weight bearing area of the medial femoral condyle using a dermal biopsy punch and manual debridement. All calcified cartilage was carefully removed with a curette, exposing the subchondral bone plate. Each specimen then underwent surgical microfracture using a 0.9 mm Kirschner wire tapped into the subchondral bone with a mallet to a depth of approximately 3 mm, with bleeding from each microfracture hole visually confirmed. Three microfracture holes were created within each full-thickness chondral defect in a triangular configuration. Once the microfracture was completed, the patella was reduced, the joint capsule was closed with interrupted sutures, and the wound was closed in anatomical layers. Postoperatively the animals were allowed to move freely within their cages Immediately after surgery, the rabbits were randomly divided into two groups of 4 rabbits each. Group 1 rabbits received a weekly injection of the therapeutic agent, and group 2 rabbits received a weekly injection of the control HMWHA formulation, for three weeks starting immediately after surgery.

Gross Anatomical and Histological Assessment of Cartilage Repair.

At the time of harvest (3 months post-microfracture surgery), the knee was approached through a medial parapatellar incision with the patella dislocated laterally. Gross assessment of the microfractured areas was performed by two blinded observers, using a modified component of the International Cartilage Repair Society (ICRS) Cartilage Repair Assessment scoring scale (macroscopic appearance subcategory) (17). After gross inspection, the operative knee was harvested and fixed in formalin and decalcified with formic acid. Histological analysis of safranin O-stained sections (6 μm thick) of the repair tissue was performed for each specimen by two blinded observers, with attention paid to the overall appearance of the repair tissue, cell shape, the extent of defect filling, and the integration with the defect edges. Additionally, the surrounding cartilage immediately outside the repaired defect (adjacent articular cartilage) was assessed histologically. All histological specimens were scored according a modified International Cartilage Repair Society (ICRS) histological cartilage scoring system (18). For each knee joint 5 sections spaced 50 µm apart were scored; the score for one knee joint consists of the average score for these sections.

Chondrocyte Cultures and Analysis of RHAMM mRNA Levels.

Chondrocytes were isolated from articular cartilage of 5—day-old mice as described previously (20). Cells were plated at high density, which maintains their chondrocytic phenotype (21), and at low density, which promotes their de-differentiation, and grown in monolayer cultures in Dulbecco's modified Eagle's medium (DMEM; Life Technologies, Gaithersburg, Md.) containing 10% fetal calf serum (FCS; HyClone, Logan, Utah), 2 mM L-glutamine (Invitrogen, Carlsbad, Calif.), and 50 U/m 1 of penicillin and streptomycin (Invitrogen) (complete medium). Chondrocyte cultures at high density were switched to serum-free medium after 3 days for 24 h followed by treatment 10 ng/ml recombinant mouse interleukin-1beta (IL-1β) (R & D Systems, Minneapolis, Minn.) in PBS/0.1% BSA for 6 h. Control cultures were treated with PBS/0.1% BSA (vehicle).

To determine the mRNA levels of RHAMM in these cultures, total RNA was isolated and reverse transcribed into cDNA. A 1:100 dilution of the resulting cDNA was used as a template to quantify the relative content of mRNA by real-time PCR with appropriate primers and SYBR Green. The 18S RNA was amplified at the same time and used as an internal control. The cycle threshold values for 18S RNA and the samples were measured and calculated by computer software.

Statistical Analysis.

The data are expressed as mean with 95% confidence intervals and were analyzed using one-way analysis of the variance (ANOVA). When ANOVA showed significant differences between the groups, Tukey's post hoc test was used to determine the pairs of groups showing significant differences. P value of <0.05 was considered statistically significant.

Results

Figure 3:
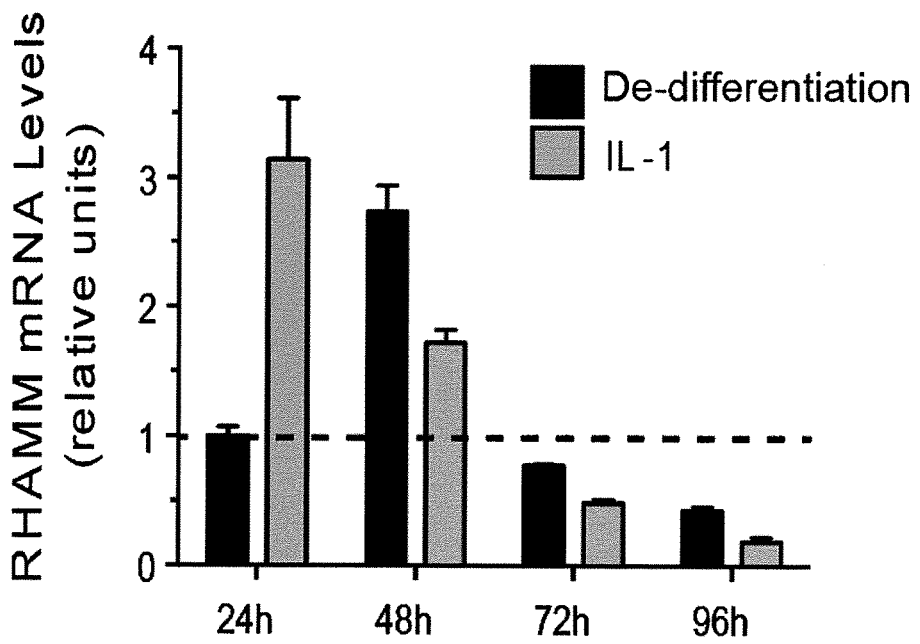
FIG. 3: Mouse articular chondrocytes express RHAMM as determined by real time PCR. When mouse articular chondrocytes were cultured in the presence of IL-1 (inflammatory conditions) RHAMM mRNA levels were markedly increased after 24 h and 48 h (grey bars) compared to untreated cells. When mouse articular chondrocytes were cultured under conditions that caused their de-differentiation into a fibroblast-like phenotype, RHAMM mRNA levels were markedly increased after 48 h (black bars) compared to untreated differentiated cells. RHAMM mRNA levels were determined by real time PCR using SYBR Green and normalized to the 18S RNA. mRNA levels are expressed as relative units with the mRNA levels of untreated cells set as 1 for each time point (indicated by dotted line). Data are expressed as mean+SD from the results of three different cultures.

We determined that articular chondrocytes express the RHAMM receptor. We cultured mouse articular chondrocytes under inflammatory conditions in the presence of interleukin-1beta (IL-1β) for up to 96 h and determined the mRNA levels of RHAMM in these cultures using real time PCR analyses. Interestingly, IL-1β treatment markedly upregulated RHAMM mRNA levels at 24 h and 48 h compared to untreated cells (FIG. 3, grey bars). In addition, RHAMM mRNA levels were markedly upregulated 48 h after mouse articular chondrocytes were cultured under conditions that cause these cells to de-differentiate into fibroblast-like cells (FIG. 3, black bars).

Figure 4:
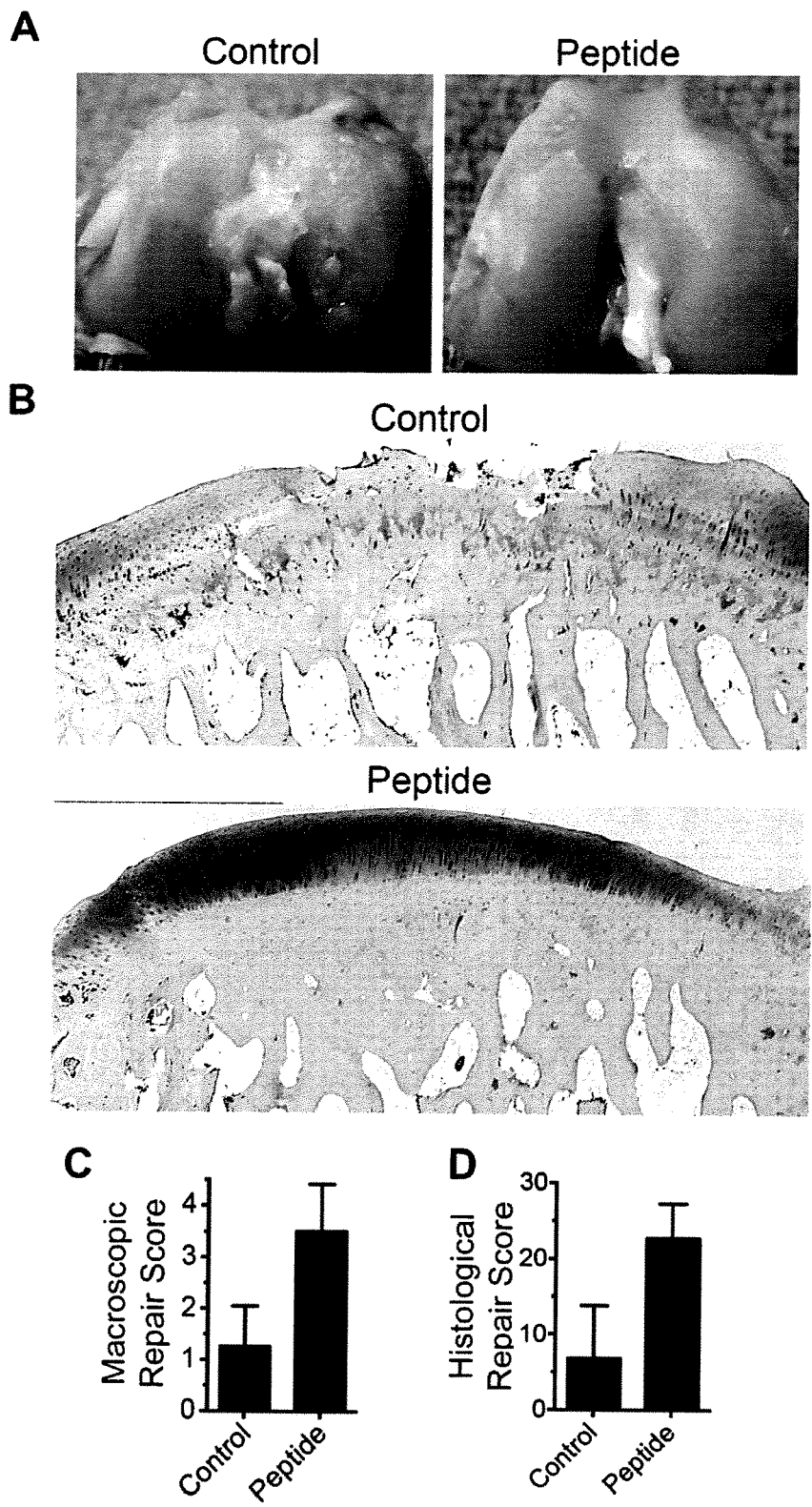
FIG. 4: Macroscopic (A) and histological (B) analyses of the repair of 4 mm full-thickness cartilage defects after microfracture surgery and injection of peptide 15-1 in HMWHA (Peptide) or HMWHA alone (Control). Full-thickness cartilage defects and microfracture surgery followed by three weekly injections of peptide 15-1 in HMWHA or HMWHA alone were performed in the weight bearing area of rabbit medial femoral condyles. Macroscopic and histological analyses of the repair of these defects were performed as described in the Methods. A: Macroscopic appearance of the defects 3 months after surgery. B: Histological appearance of repaired tissue 3 months post-operatively with safranin O staining. (C): Macroscopic grading of the repaired tissue in the defect site at 3 months postoperatively. (D): Histological grading of the repaired tissue at 3 months postoperatively. The results represent the mean with 95% CI (two groups of 4 rabbits each). Data were analyzed using one-way ANOVA followed by Tukey's post hoc test.

To determine the effect of peptide 15-1 on cartilage repair in rabbits, we created 4 mm-sized full-thickness cartilage defects in the weight bearing area of the medial femoral condyle. We then created three micro-fracture holes in the defect area. Rabbits were divided into two groups with 4 rabbits in each group. One group received three weekly intra-articular injections of therapeutic agent (6 mg HMWHA and 0.1 mg peptide 15-1) starting immediately after surgery, whereas the other group (control group) received three weekly injections of 6 mg HMWHA. Macroscopic observations revealed that the rabbit joints injected with the therapeutic agent (FIG. 4A, Peptide) showed marked improvement in the repair of the defect site compared to the repair in rabbit joints injected with HMWHA (FIG. 4A, Control). Macroscopic examination of the knees revealed that the defects from the rabbits injected with therapeutic agent were filled to the level of the articular cartilage surface with a repair tissue well integrated with the surrounding cartilage. The color of the new tissue resembled that of native (hyaline) cartilage. The defect margins were barely visible (FIG. 4A, Peptide). Contrary knees from rabbits injected with HMWHA showed only very partial cartilage repair mainly restricted to the sites of the microfracture holes (FIG. 4A, Control). The regeneration of cartilage was evaluated on histological sections using safranin O staining. Histological analysis 3 months after surgery revealed a markedly better repair of the defect in knee joints injected with therapeutic agent (FIG. 4B, Peptide) compared to knee joints treated with HMWHA (FIG. 4B, Control). The results of safranin O staining revealed that the tissue regenerated in the defects of knee joints injected with therapeutic agent has viable chondrocytes arranged in lacunae structure as in native (hyaline) cartilage tissue. This regenerated cartilage has abundance of cartilage matrix denoted by the more intense safranin O staining. The matrix in the regenerated tissue is homogenously distributed. Also subchondral bone is fully regenerated. The tissue regenerated is closely integrated with the native cartilage tissue and subchondral bone below it (FIG. 4B, Peptide). Contrarily, the knee with cartilage defect that was injected with HMWHA alone showed very poor cartilage regeneration. In addition, the regenerated cartilage showed a fibrocartilage-like appearance rather than a hyaline cartilage appearance as in the repaired defects of therapeutic agent-injected knee joints (FIG. 4B, Control, Peptide). Previously described macroscopic and histological scoring systems were used to evaluate the healing of the defect sites (17, 18). Both the macroscopic and histological scores showed significant differences in the total macroscopic (p=0.0011) and histological (p=0.0016) scores of the knee joints treated with therapeutic agent compared to the knee joints injected with HMWHA (FIGS. 4C,D).

EXAMPLE 2

Methods

Chondrocyte Cultures.

Human articular chondrocytes were isolated from articular cartilage samples obtained from patients (donor age range 48-67) undergoing total knee replacement surgery at NYU Hospital for Joint Diseases. Knee cartilage was harvested from regions with no macroscopically evident degeneration. The collection of tissue from patients undergoing knee replacement surgery was approved by the Institutional Regulatory Board (IRB) at NYU School of Medicine. Human chondrocytes were isolated from these cartilage samples and cultured as described by us previously (24). Before human chondrocyte cultures were treated with inflammatory stimulus (interleukin-1beta (IL-1β), chondrocyte cultures were switched to serum-free medium for 24 h followed by treatment with the inflammatory stimulus. Cells were treated with 10 ng/ml human recombinant IL-1β in phosphate-buffered saline (PBS)/0.1% BSA. In addition, serum-starved cells were treated with RHAMM-mimetic peptide at various concentrations, HMWHA (ORTHOVISC) at a concentration of 1000 µg/ml, and a combination at four different weight ratios (1:60, 1:30, 1:15, 1:8) of peptide and HMWHA. Cells were treated with these various agents for 24 or 48 h under serum-free conditions.

The synovial fibroblast cell line SW982 was used between passage 3 and passage 7 and cultured in DMEM containing 10% fetal calf serum until the cells reached confluence. Cells were then serum-starved for 24 h and then treated with 10 ng/ml recombinant human IL-1β and 52 ng/ml RHAMM-mimetic peptide for 48 h.

RT-PCR and Real-Time PCR Analysis.

mRNA levels of catabolic markers (cyclooxygenase (Cox)-2, interleukin (IL)-6, inducible nitric oxide synthase (iNOS), matrix metalloproteinase (MMP)-13) and articular cartilage markers (aggrecan, type II collagen) were determined by real time PCR analysis as described by us previously (25, 26). Briefly, total RNA was isolated from chondrocyte cultures using the RNEASY minikit (Qiagen, Valencia, Calif.). One μg of total RNA was reverse transcribed by using an OMNISCRIPT RT kit (Qiagen). A 1:100 dilution of the resulting cDNA was used as the template to quantify the relative content of mRNA by real-time PCR (STEPONEPLUS™ System; Applied Biosystems, Foster City, Calif.) with the appropriate primers and SYBR Green. PCRs were performed with a SYBR Green PCR Master Mix kit (Applied Biosystems), at 95° C. for 10 min followed by 40 cycles at 95° C. for 15 s and 60° C. for 1 min, and 1 cycle at 95° C. for 15 s and 60° C. for 1 min. The 18S RNA was amplified at the same time and used as an internal control. The cycle threshold values for 18S RNA and the samples were measured and calculated by computer software.

Analysis of HA Concentration in Chondrocyte Culture Medium.

We collected the medium after various time periods of treatment of the different cultures for analysis of HA content. Conditioned media (approximately 1 ml each sample) from chondrocyte cultures were stored frozen at −20° C. until analyzed. Phosphate-buffered saline (PBS), phosphate-buffered saline with 0.05% (w/w) Tween 20 (PBS 0.05% Tween), Tween 20, and sodium acetate were from Sigma Chemical. The HA sandwich ELSA (Enzyme-Linked Sorbent Assay) kit DY3614, color reagents A (hydrogen peroxide) and B (tetramethylbenzidine), 96-well transparent polystyrene plates, and ELISA Ancillary Reagent Kit 1 were from R&D Systems.

Based on preliminary studies, the dilutions needed for each sample were planned. For the sandwich assay ELSA, the first dilution was chosen with a goal of having the HA concentration in the range of 50-90 ng/ml. Subsequent dilutions were made serially, from the first dilution. Before use, each frozen sample was kept at room temperature for approximately 15 min to melt. For the sandwich assay, dilutions were made with R & D Systems "Reagent Diluent", supplied as a concentrated stock solution in the ELISA Ancillary Reagent Kit 1, or equivalently, lab-prepared PBS containing 5% Tween 20, filtered through a 0.2 μm pore filter. The sandwich ELSA assay was performed according to the instructions supplied by the kit manufacturer (27).

Results

Figure 5:
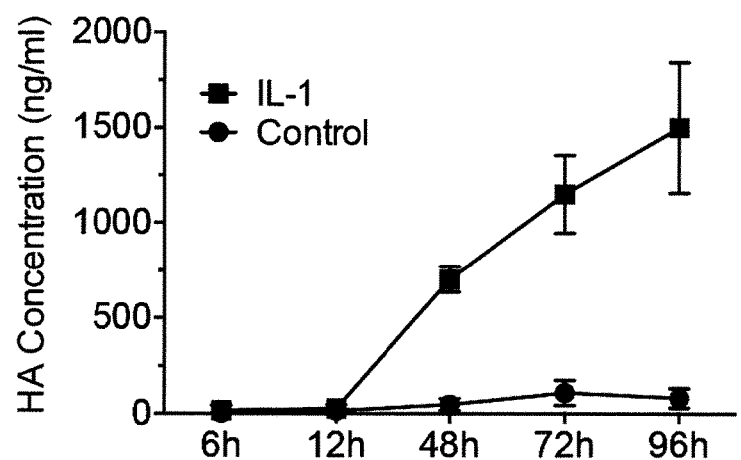
FIG. 5: The amount of HA released into the medium increased in IL-1β-treated human articular chondrocytes in a time-dependent manner. Human articular chondrocytes were serum-starved for 24 h followed by treatment with 10 ng/ml IL-1β for various time periods (6, 12, 48, 72 and 96 hours). Control cells were treated with PBS/0.1% bovine serum albumin (BSA). Medium was collected after the time points indicated and the HA concentration was analyzed using an ELSA (ELISA-like) specific assay.
Figure 7:
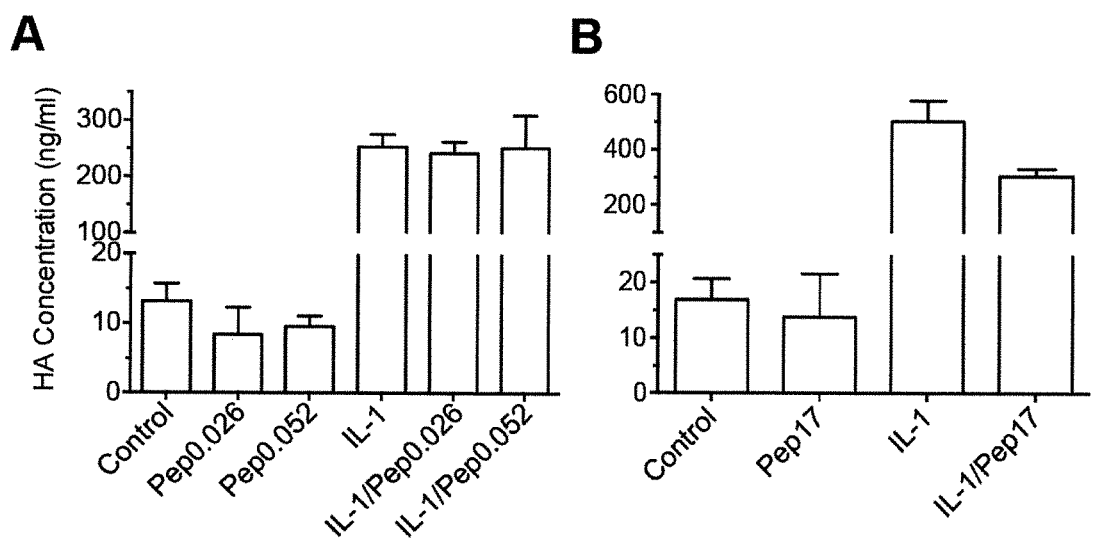
FIG. 7: HA concentration in the medium of human articular chondrocytes is increased by IL-1β. A: RHAMM-mimetic peptide at a concentration of 0.026 µg/ml or 0.052 µg/ml (Pep0.026, Pep0.052) had no effect on the HA release into the medium of IL-1β-treated chondrocytes. B: The RHAMM-mimetic peptide at a higher concentration of 17 µg/ml (Pep17) significantly reduced HA concentration released into the medium of IL-1β-treated chondrocytes. Human articular chondrocytes were serum-starved for 24 h followed by treatment of these cells with 10 ng/ml IL-1β and various concentrations of the RHAMM-mimetic peptide for 48 h. HA released into the medium was measured by ELSA (ELISA-like) specific assay.

Cartilage injury and repair leads to an inflammatory environment that is hostile for the repair and healing process. One of the major inflammatory cytokines released in cartilage injury and repair is IL-1β (22). We and others have shown that treatment of human articular chondrocytes with IL-1β (10 ng/ml) for 24 h resulted in a marked increase of the mRNA levels of catabolic markers (Cox-2, IL-6, iNOS, MMP-13) and a decrease in the mRNA levels of articular cartilage markers (aggrecan, type II collagen; see FIG. 7) (23). In addition, IL-1β treatment resulted in an increase of HA released into the medium in human articular chondrocytes compared to vehicle (PBS/0.1% BSA)-treated cells (FIG. 5). The amounts of HA released into the medium increased over time and reached its highest level after 96 h IL-1β treatment (FIG. 5, square). The HA amount in the medium was little altered in vehicle-treated cells over time (FIG. 5, circle).

Figure 6:
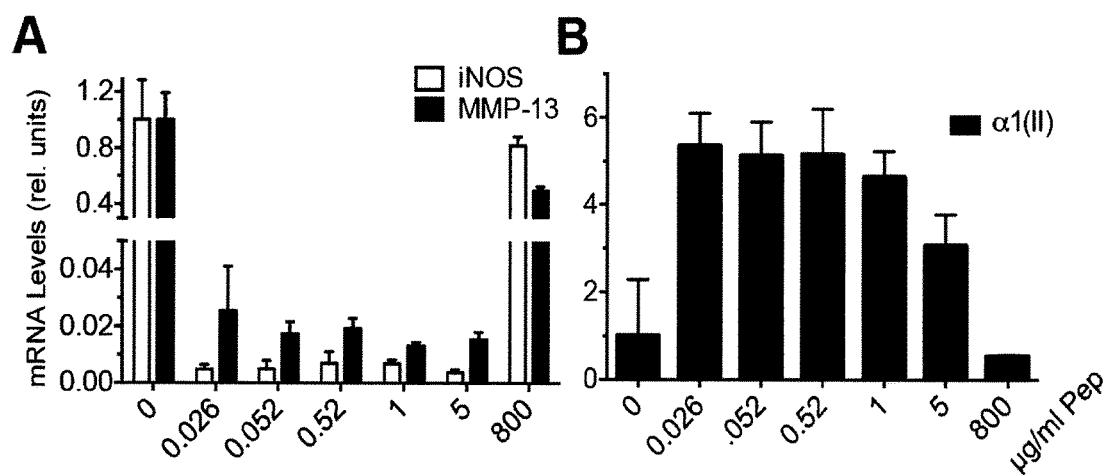
FIG. 6: RHAMM-mimetic peptide at concentrations up to 5 µg/ml decreased the mRNA levels of iNOS and MMP-13 (catabolic markers; A) and increased the mRNA levels of type II collagen (α1(II), articular cartilage marker, B) in serum-starved human articular chondrocytes. At 800 µg/ml the peptide was not as effective in decreasing the mRNA levels of the catabolic markers as lower concentrations of the peptide. In addition, 800 µg/ml of peptide decreased the mRNA levels of type II collagen. Human articular chondrocytes after being serum-starved for 24 h were treated with RHAMM-mimetic peptide of SEQ ID NO:1 (Pep.) at various concentrations (0, 26, 52, 520, 1000, 5000 ng/ml) for 48 h. mRNA levels of iNOS, MMP-13, and type II collagen were determined by real time PCR using SYBR Green and normalized to the 18S RNA. mRNA levels are expressed as relative units with the mRNA levels of untreated cells set as 1. Data are expressed as mean±SD from the results of three different cultures.

In the next set of experiments, it was determined whether the RHAMM-mimetic peptide of SEQ ID NO:1 was able to reduce the expression of catabolic markers and increase the expression of articular cartilage markers in serum-starved human articular chondrocytes. Serum-starved human articular chondrocytes were treated with various concentrations (0.026, 0.052, 0.520, 1, 5, 800 μg/ml) of the RHAMM-mimetic peptide for 48 h. The peptide decreased the mRNA levels of catabolic markers (iNOS, MMP-13) at all concentrations of the peptide tested (FIG. 6A). The peptide at concentrations up to 5 μg/ml increased the mRNA levels of articular cartilage marker, type II collagen (FIG. 6B). At a concentration of 800 μg/ml the peptide decreased the mRNA level of type II collagen compared to untreated cells (FIG. 6B). These findings demonstrate that the peptide at concentrations below 800 μg/ml is effective in inhibiting catabolic events and stimulation of the expression of articular cartilage markers in human articular chondrocytes (FIG. 6). The peptide also moderated the increase in the level of HA in conditioned media after treatment with IL-1β. Low peptide concentration of 26 ng/ml or 52 ng/ml had little effect (FIG. 7A), but the peptide at a concentration of 17 μg/ml significantly reduced the increase in HA concentration caused by IL-1β (FIG. 7B).

Figure 8:
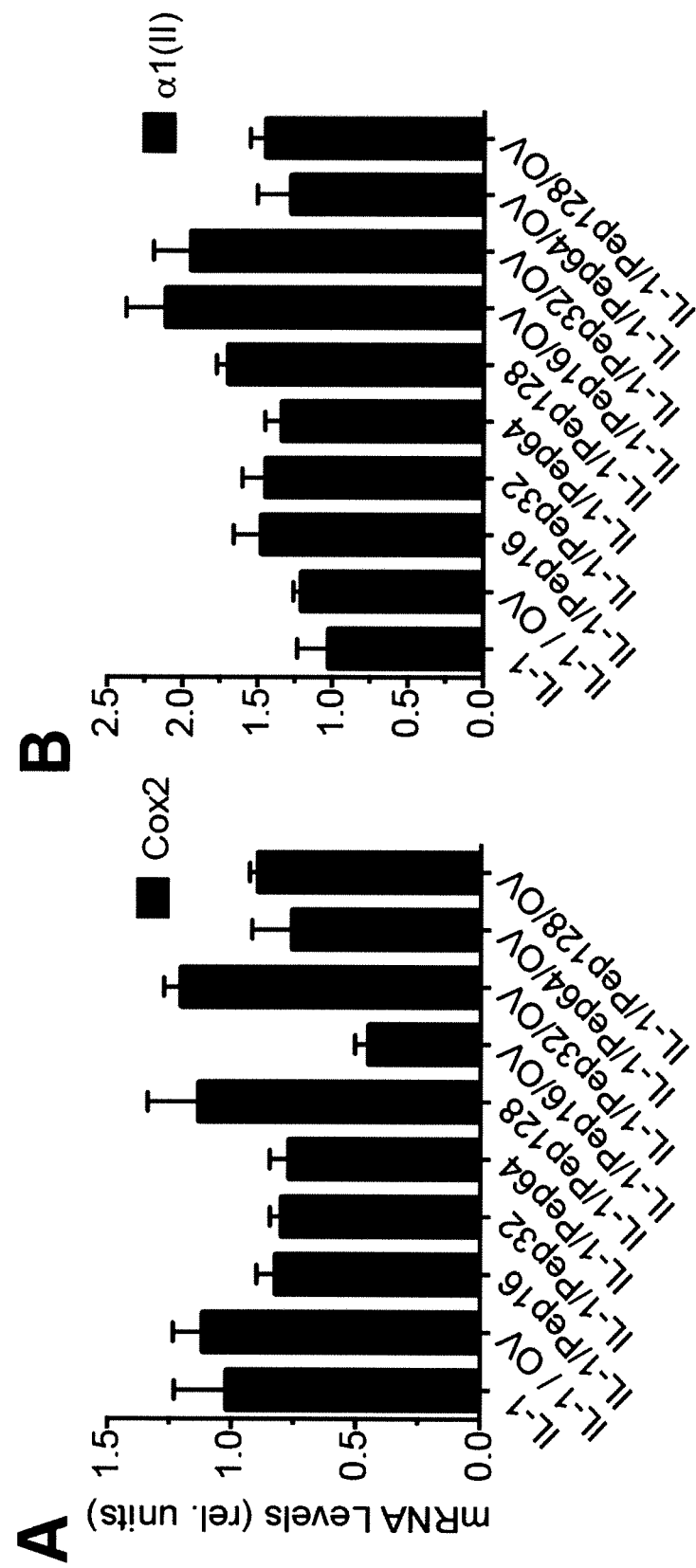
FIG. 8: RHAMM-mimetic peptide at concentrations (16, 32, 64 µg/ml) decreased the mRNA levels of Cox-2 (catabolic marker; A) and increased the mRNA levels of type II collagen (α1 (II), articular cartilage marker, B) in IL-1β-treated human articular chondrocytes. HMWHA (ORTHO-VISC, OV (a commercially available high molecular weight HA) treatment did not affect the mRNA levels of Cox-2 and type II collagen in IL-1β-treated human articular chondrocytes. HMWHA together with the peptide was more effective in decreasing Cox-2 mRNA levels and increasing type II collagen mRNA levels in IL-1β-treated human articular chondrocytes than peptide alone, with peptide and HMWHA at a weight ratio of 1:60 (peptide concentration 16 µg/ml) being the most effective. Human articular chondrocytes after being serum-starved for 24 h were treated with RHAMM-mimetic peptide (Pep) at various concentrations (16, 32, 64, 128 µg/ml), HA (OV) at a concentration of 1 mg/l, or peptide and OV mixed at various ratios, and 10 ng/ml human recombinant IL-1β for 24 h. mRNA levels of Cox-2 and type II collagen were determined by real time PCR using SYBR Green and normalized to the 18S RNA. mRNA levels are expressed as relative units with the mRNA levels of untreated cells set as 1. Data are expressed as mean±SD from three different cultures.

Since cartilage injury and repair leads to an inflammatory environment and IL-1β is one of the major cytokines in this inflammatory environment (22), it was determined whether the peptide is chondro-protective and inhibits catabolic events in chondrocytes in an inflammatory environment. In addition, it was determined whether high molecular weight HA (HMWHA, ORTHOVISC, 1 mg/ml) together with the peptide act synergistically on articular chondrocytes in an inflammatory environment (+IL-1β). Serum-starved human articular chondrocytes were treated with 1 mg/ml HMWHA (ORTHOVISC, OV) or peptide at different concentrations (16, 32, 64, 128 μg/ml) in the presence of 10 ng/ml IL-1β for 24 h. In addition, we treated chondrocytes with a mixture of HMWHA and RHAMM-mimetic peptide in different ratios. For cartilage repair in rabbits, a ratio of peptide to HMWHA of 1:60 was used. In the in vitro experiments the following ratios: 1:60, 1:30, 1:15, and 1:8 were used. Cells were cultured in the presence of peptide, HMWHA, or HMWHA and peptide at the different ratios and IL-1β at 10 ng/ml for 24 h. mRNA levels of Cox-2 (catabolic marker) and type II collagen (articular cartilage marker) were measured. HMWHA (OV) at a concentration of 1 mg/ml did not alter the mRNA levels of Cox-2 and type II collagen in IL-1β-treated human articular chondrocytes (FIG. 8A, B). The RHAMM-mimetic peptide at concentrations up to 64 μg/ml decreased the mRNA levels of Cox-2 (FIG. 8A) and increased the mRNA level of type II collagen (FIG. 8B). HMWHA and the peptide together were more effective in decreasing the mRNA levels of Cox-2 and increasing type II collagen mRNA levels in IL-1β-treated chondrocytes than the peptide alone (FIG. 8A, B). Similar to the in vivo cartilage repair experiments, the peptide to HMWHA ratio of 1:60 (Pep 16/OV) was the most effective ratio in decreasing Cox-2 mRNA levels and increasing type II collagen mRNA levels. These findings support synergistic action of HMWHA and the RHAMM-mimetic peptide in cartilage defect repair.

Figure 9:
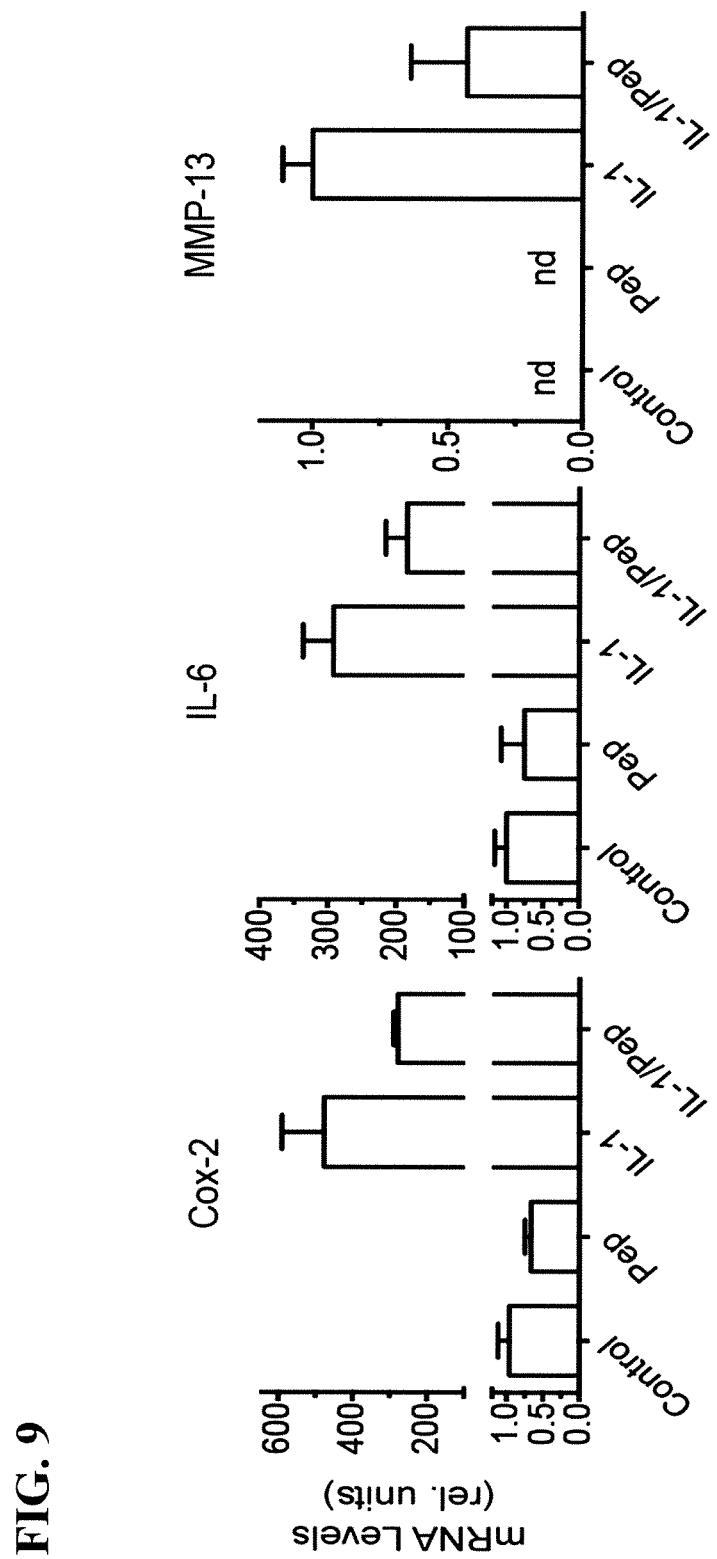
FIG. 9: RHAMM-mimetic peptide decreased the mRNA levels of catabolic markers (Cox-2, IL-6, MMP-13) in the SW982 synovial cell line. SW982 cells after being serum-starved for 24 h were treated with RHAMM-mimetic peptide of SEQ ID NO:1 (Pep) at a concentration of 52 ng/ml for 24 h. mRNA levels of Cox-2, IL-6 and MMP-13 were determined by real time PCR using SYBR Green and normalized to the 18S RNA. mRNA levels are expressed as relative units with the mRNA levels of untreated cells set as 1. Data are expressed as mean±SD from the results of three different cultures.

Since cartilage injury and repair not only affect cartilage but also involve the other joint tissues, including the synovium and synovial fibroblasts, it was determined how the RHAMM-mimetic peptide affects the expression of catabolic markers (Cox-2, IL-6, MMP-13) in IL-1β-treated synovial fibroblasts. For these experiments, synovial fibroblast cell line SW982 was used. Cells were serum-starved for 24 h followed by treatment with 10 ng/ml human recombinant IL-1β and 52 ng/ml RHAMM-mimetic peptide for 24 h. IL-1β increased the mRNA levels of Cox-2, IL-6 and MMP-13 in these cells (FIG. 9). The peptide markedly reduced the mRNA levels of these catabolic markers in IL-1β-treated SW982 cells (FIG. 9). These findings show that the RHAMM-mimetic peptide reduces the expression of catabolic markers in synovial fibroblasts and articular chondrocytes when cultured in an inflammatory environment.

In summary, the RHAMM-mimetic peptide decreased the expression levels of catabolic markers and increased the expression levels of articular cartilage markers in human articular chondrocytes in a non-inflammatory and inflammatory environment. In addition, an inflammatory environment markedly increased the amounts of HA released into the medium of human articular chondrocytes. The RHAMM-mimetic peptide decreased the amounts of HA released into the medium in IL-1β-treated human articular chondrocytes. Finally, the peptide and HMWHA affected IL-1β-treated human articular chondrocytes synergistically to reduce catabolic events and stimulate the expression of articular cartilage markers.

Methods:

Chondrocyte Cultures.

Human articular chondrocytes were isolated from articular cartilage samples obtained from patients (donor age range 48-67) undergoing total knee replacement surgery at NYU Hospital for Joint Diseases. Knee cartilage was harvested from regions with no macroscopically evident degeneration. The collection of tissue from patients undergoing knee replacement surgery was approved by the Institutional Regulatory Board (IRB) at NYU School of Medicine. Human chondrocytes were isolated from these cartilage samples and cultured as described by us previously (24). Before human chondrocyte cultures were treated with inflammatory stimulus (interleukin-1beta (IL-1β), chondrocyte cultures were switched to serum-free medium for 24 h followed by treatment with the inflammatory stimulus. Cells were treated with 10 ng/ml human recombinant IL-1β in phosphate-buffered saline (PBS)/0.1% BSA. In addition, serum-starved cells were treated with RHAMM-mimetic peptide at various concentrations, HMWHA (ORTHOVISC) at a concentration of 1000 μg/ml, and a combination at four different weight ratios (1:60, 1:30, 1:15, 1:8) of peptide and HMWHA. Cells were treated with these various agents for 24 or 48 h under serum-free conditions.

The synovial fibroblast cell line SW982 was used between passage 3 and passage 7 and cultured in DMEM containing 10% fetal calf serum until the cells reached confluence. Cells were then serum-starved for 24 h and then treated with 10 ng/ml recombinant human IL-1β and 52 ng/ml RHAMM-mimetic peptide for 48 h.

RT-PCR and Real-Time PCR Analysis.

mRNA levels of catabolic markers (cyclooxygenase (Cox)-2, interleukin (IL)-6, inducible nitric oxide synthase (iNOS), matrix metalloproteinase (MMP)-13) and articular cartilage markers (aggrecan, type II collagen) were determined by real time PCR analysis as described by us previously (25, 26). Briefly, total RNA was isolated from chondrocyte cultures using the RNEASY minikit (Qiagen, Valencia, Calif.). One μg of total RNA was reverse transcribed by using an OMNISCRIPT RT kit (Qiagen). A 1:100 dilution of the resulting cDNA was used as the template to quantify the relative content of mRNA by real-time PCR (STEPONEPLUS™ System; Applied Biosystems, Foster City, Calif.) with the appropriate primers and SYBR Green. PCRs were performed with a SYBR Green PCR Master Mix kit (Applied Biosystems), at 95° C. for 10 min followed by 40 cycles at 95° C. for 15 s and 60° C. for 1 min, and 1 cycle at 95° C. for 15 s and 60° C. for 1 min. The 18S RNA was amplified at the same time and used as an internal control. The cycle threshold values for 18S RNA and the samples were measured and calculated by computer software.

Analysis of HA Concentration in Chondrocyte Culture Medium.

We collected the medium after various time periods of treatment of the different cultures for analysis of HA content. Conditioned media (approximately 1 ml each sample) from chondrocyte cultures were stored frozen at −20° C. until analyzed. Phosphate-buffered saline (PBS), phosphate-buffered saline with 0.05% (w/w) Tween 20 (PBS 0.05% Tween), Tween 20, and sodium acetate were from Sigma Chemical. The HA sandwich ELSA (Enzyme-Linked Sorbent Assay) kit DY3614, color reagents A (hydrogen peroxide) and B (tetramethylbenzidine), 96-well transparent polystyrene plates, and ELISA Ancillary Reagent Kit 1 were from R & D Systems.

Based on preliminary studies, the dilutions needed for each sample were planned. For the sandwich assay ELSA, the first dilution was chosen with a goal of having the HA concentration in the range of 50-90 ng/ml. Subsequent dilutions were made serially, from the first dilution. Before use, each frozen sample was kept at room temperature for approximately 15 min to melt. For the sandwich assay, dilutions were made with R & D Systems "Reagent Diluent", supplied as a concentrated stock solution in the ELISA Ancillary Reagent Kit 1, or equivalently, lab-prepared PBS containing 5% Tween 20, filtered through a 0.2 μm pore filter. The sandwich ELSA assay was performed according to the instructions supplied by the kit manufacturer (27).

While the invention has been described through examples and various embodiments, it will be apparent to those skilled in the art that routine modifications can be made, and such modifications are intended to be within the scope of the disclosure.

REFERENCES

1. Curl W W, Krome J, Gordon E S, Rushing J, Smith B P, Poehling G G 1997 Cartilage injuries: a review of 31,516 knee arthroscopies. Arthroscopy: the journal of arthroscopic & related surgery: official publication of the Arthroscopy Association of North America and the International Arthroscopy Association 13(4):456-60.
2. Farr J, Cole B, Dhawan A, Kercher J, Sherman S 2011 Clinical cartilage restoration: evolution and overview. Clin Orthop Relat Res 469(10):2696-705.
3. Buckwalter J A, Brown T D 2004 Joint injury, repair, and remodeling: roles in post-traumatic osteoarthritis. Clin Orthop Relat Res (423):7-16.
4. Redler L H, Caldwell J M, Schulz B M, Levine W N 2012 Management of articular cartilage defects of the knee. The Physician and sportsmedicine 40(1):20-35.

5. von der Mark K 1986 Differentiation, modulation and dedifferentiation of chondrocytes. Rheumatology 10:72-315.
6. Hunziker E B, Stahli A 2008 Surgical suturing of articular cartilage induces osteoarthritis-like changes. Osteoarthritis Cartilage 16(9):1067-73.
7. Kuettner K E, Aydelotte M B, Thonar E J M A 1991 Articular cartilage matrix and structure: a minireview. J. Rheumato. Suppl. 27:46-48.
8. Schmidt T A, Gastelum N S, Nguyen Q T, Schumacher B L, Sah R L 2007 Boundary lubrication of articular cartilage: role of synovial fluid constituents. Arthritis Rheum 56(3):882-91.
9. Kwiecinski J J, Dorosz S G, Ludwig T E, Abubacker S, Cowman M K, Schmidt T A 2011 The effect of molecular weight on hyaluronan's cartilage boundary lubricating ability—alone and in combination with proteoglycan 4. Osteoarthritis Cartilage 19(11):1356-62.
10. Lotz M 2012 Osteoarthritis year 2011 in review: biology. Osteoarthritis Cartilage 20(3):192-6.
11. Rutjes A W, Juni P, da Costa B R, Trelle S, Nuesch E, Reichenbach S2012 Viscosupplementation for osteoarthritis of the knee: a systematic review and meta-analysis. Ann Intern Med 157(3):180-91.
12. Balazs E A, Denlinger J L 1993 Viscosupplementation: a new concept in the treatment of osteoarthritis. The Journal of rheumatology. Supplement 39:3-9.
13. Gomis A, Pawlak M, Balazs E A, Schmidt R F, Belmonte C 2004 Effects of different molecular weight elastoviscous hyaluronan solutions on articular nociceptive afferents. Arthritis Rheum 50(1):314-26.
14. Balazs E A 2003 Analgesic effect of elastoviscous hyaluronan solutions and the treatment of arthritic pain. Cells, tissues, organs 174(1-2):49-62.
15. Balasz E A, Band P A 2008 Therapeutic Use of Hyaluronan-Based Products. In: Garg H G, Cowman M K, Hales C A (eds.) Carbohydrate Chemistry, Biology and Medical Applications. Elsevier, Amsterdam, pp 311-332.
16. Tolg C, Hamilton S R, Zalinska E, McCulloch L, Amin R, Akentieva N, Winnik F, Savani R, Bagli D J, Luyt L G, Cowman M K, McCarthy J B, Turley E A 2012 A RHAMM Mimetic Peptide Blocks Hyaluronan Signaling and Reduces Inflammation and Fibrogenesis in Excisional Skin Wounds. Am J Pathol 181(4):1250-70.
17. Brittberg M, Winalski C S 2003 Evaluation of cartilage injuries and repair. The Journal of bone and joint surgery. American volume 85-A Suppl 2:58-69.
18. Mainil-Varlet P, Aigner T, Brittberg M, Bullough P, Hollander A, Hunziker E, Kandel R, Nehrer S, Pritzker K, Roberts S, Stauffer E, International Cartilage Repair S 2003 Histological assessment of cartilage repair: a report by the Histology Endpoint Committee of the International Cartilage Repair Society (ICRS). The Journal of bone and joint surgery. American volume 85-A Supp 12:45-57.
19. Strauss E, Schachter A, Frenkel S, Rosen J 2009 The efficacy of intra-articular hyaluronan injection after the microfracture technique for the treatment of articular cartilage lesions. The American journal of sports medicine 37(4):720-6.
20. Lefebvre V, Garofalo S, Zhou G, Metsaranta M, Vuorio E, DeChrombrugghe B 1994 Characterization of primary cultures of chondrocytes from type II collagen/beta-galactosidase transgenic mice. Matrix Biol. 14:329-335.
21. Zhu M, Tang D, Wu Q, Hao S Rosier R N, O'Keefe R J, Zuscik M, Chen D 2009 Activation of beta-catenin signaling in articular, Chen M, Xie C, chondrocytes leads to osteoarthritis-like phenotype in adult beta-catenin conditional activation mice. J Bone Miner Res 24(1):12-21.
22. Furman, B. D., Mangiapani, D. S., Zeitler, E., Bailey, K. N., Home, P. H., Huebner, J. L., Kraus, V. B., Guilak, F., and Olson, S. A. (2014) Targeting pro-inflammatory cytokines following joint injury: acute intra-articular inhibition of interleukin-1 following knee injury prevents post-traumatic arthritis. *Arthritis research & therapy* 16, R134
23. Oliviero, F., Ramonda, R., and Punzi, L. (2010) New horizons in osteoarthritis. *Swiss medical weekly* 140, w13098
24. von der Mark, K., Kirsch, T., Nerlich, A., Kuss, A., Weseloh, G., and Gluckert, K. (1992) Type X collagen synthesis in human osteoarthritic cartilage. Indication of chondrocyte hypertrophy. *Arth. Rheum.* 35, 806-811
25. Campbell, K. A., Minashima, T., Zhang, Y., Hadley, S., Lee, Y. J., Giovinazzo, J., Quirno, M., and Kirsch, T. (2013) Annexin A6 Interacts With p 65 and Stimulates NF-kappaB Activity and Catabolic Events in Articular Chondrocytes. *Arthritis and rheumatism* 65, 3120-3129
26. Wang, W., and Kirsch, T. (2002 Jun. 10) Retinoic acid stimulates annexin-mediated growth plate chondrocyte mineralization. *The Journal of cell biology* 157, 1061-1069
27. Yuan, H., Tank, M., Alsofyani, A., Shah, N., Talati, N., LoBello, J. C., Kim, J. R., Oonuki, Y., de la Motte, C. A., and Cowman, M. K. (2013) Molecular mass dependence of hyaluronan detection by sandwich ELISA-like assay and membrane blotting using biotinylated hyaluronan binding protein. *Glycobiology* 23, 1270-1280.
28. Mithoefer K, McAdams T, Williams R J, Kreuz P C, Mandelbaum B R "Clinical Efficacy of the Microfracture Technique for Articular Cartilage Repair in the Knee: An Evidence Based Systematic Analysis". Am J. Sports Med. 2009. 37(10):2053-2063.

The invention claimed is:

1. A method for repairing a defect in a cartilage of a joint in a subject comprising performing a surgical procedure at a site of the defect in the cartilage, and administering: i.) a composition comprising a RHAMM-mimetic peptide and a high molecular weight hyaluronan (HMWHA) to the site of the defect in the cartilage, or
   ii. a composition comprising a RHAMM-mimetic peptide and a composition comprising high molecular weight hyaluronan (HMWHA) to the site of the defect in the cartilage, wherein the RHAMM-mimetic peptide and the HMWHA are administered in a ratio of from 1:1 to 1:1000 by weight.

2. The method of claim 1, wherein the RHAMM-mimetic peptide composition and the HMWHA composition of ii) are administered concurrently or sequentially.

3. The method of claim 1, wherein the administration is carried out via intra-articular injection.

4. The method of claim 1, wherein the surgical procedure is a microfracture.

5. The method of claim 1, wherein the RHAMM-mimetic peptide comprises the sequence of SEQ ID NO: 1.

6. The method of claim 1, wherein the HMWHA has an average molecular weight of at least 500 kDa.

7. The method of claim 1, wherein the concentration of HMWHA is from 1 mg/ml to 40 mg/ml.

8. The method of claim 1, wherein the concentration of the RHAMM-mimetic peptide is from 5 µg/ml to 3 mg/ml.

9. The method of claim 1, further comprising repeating the administration of the composition or i) or ii) to the site of the cartilage defect.

10. The method of claim 1, further comprising administering autologous mesenchymal stem cells to the site of the cartilage defect.

* * * * *